United States Patent [19]

Eibl et al.

[11] Patent Number: 5,626,867
[45] Date of Patent: May 6, 1997

[54] LIPOSOMES WITH A NEGATIVE EXCESS CHARGE

[75] Inventors: Hansjörg Eibl, Bovenden-Eddigehausen; Petra Kaufmann-Kolle, Gleichen-Diemarden; Anneliese Kranich, Freiburg; Clemens Unger, Göttingen, all of Germany

[73] Assignee: Max-Planck Gesellschaft zur Forderung der Wissenschaften E.V., Munich, Germany

[21] Appl. No.: 295,797

[22] PCT Filed: Mar. 16, 1993

[86] PCT No.: PCT/EP93/00605

§ 371 Date: Feb. 15, 1995

§ 102(e) Date: Feb. 15, 1995

[87] PCT Pub. No.: WO93/18749

PCT Pub. Date: Sep. 30, 1993

[30] Foreign Application Priority Data

Mar. 17, 1992 [DE] Germany ............ 42 08 527.6

[51] Int. Cl.[6] .................. A61K 9/14; A61K 9/127
[52] U.S. Cl. ................. 424/450; 264/41; 264/4.3
[58] Field of Search .............. 424/450; 264/4.1, 264/4.2

[56] References Cited

U.S. PATENT DOCUMENTS

| | | | |
|---|---|---|---|
| 4,186,183 | 1/1980 | Steck et al. | 424/38 |
| 4,917,897 | 4/1990 | Augustein et al. | 424/450 |
| 4,938,965 | 7/1990 | Shek et al. | 424/450 |
| 5,043,165 | 8/1991 | Radhakrishnan | 424/450 |
| 5,049,391 | 9/1991 | Suzuki et al. | 424/450 |
| 5,049,392 | 9/1991 | Weiner et al. | 424/450 |
| 5,169,636 | 12/1992 | Nanba et al. | 424/450 |
| 5,169,637 | 12/1992 | Lenk et al. | 424/450 |
| 5,192,549 | 3/1993 | Barenolz et al. | 424/450 |
| 5,204,112 | 4/1993 | Hope et al. | 124/450 |
| 5,387,410 | 2/1995 | Bosworth et al. | 424/9 |

FOREIGN PATENT DOCUMENTS

| | | |
|---|---|---|
| 0099068 | 1/1984 | European Pat. Off. . |
| 0133508 | 7/1984 | European Pat. Off. . |
| 0102324 | 3/1984 | Germany . |
| 3825374A1 | 2/1990 | Germany . |

OTHER PUBLICATIONS

Scott et al. Concise Encyclopedia Biochemistry, Second edition, p. 452 (1988).

WO 88/07362, published Oct. 6, 1988.

Tokumura et al, Arzneim–Forsch./Drug Res., "Effects of Lysophosphatidic Acids and their Structural Analogs on Arterial Blood Pressure of Cats", 35(I), Nr. 3 (1985).

Buri et al., Technique et Documentation, "formes Pharmaceutiques Nouvelles", (1985).

*Primary Examiner*—Jeff Mullis
*Attorney, Agent, or Firm*—Nikaido, Marmelstein, Murray & Oram LLP

[57] ABSTRACT

The present invention concerns liposomes with a negative excess charge and pharmaceutical compositions produced therefrom. The liposomes contain 30 to 50 mol % cholesterol, 49 to 56 mol % phospholipids and 1 to 14 mol % of one or several compounds of the general formula I

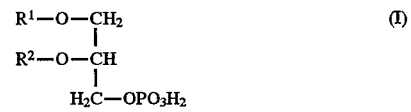

or salts thereof in relation to the total lipid components of the liposomes, in which $R^1$ and $R^2$ are the same or different and represent hydrogen, $C_1$–$C_4$ alkyl groups or saturated or unsaturated $C_8$–$C_{24}$ acyl groups which are unbranched or branched or/and unsubstituted or substituted, provided that at least one of the residues $R^1$ and $R^2$ is an acyl group as defined above. A process for the production of the liposomes in accordance with the invention is also provided.

19 Claims, No Drawings

LIPOSOMES WITH A NEGATIVE EXCESS CHARGE

DESCRIPTION

The invention concerns liposomes with a negative excess charge, in particular for administering cytostatic agents and cytokines.

Liposomes are spherical structures comprising one or several lipid double layers with an aqueous inner space (lipid vesicle). Such vesicles can be produced by the mechanical very fine dispersion of phospholipids (e.g. lecithin) in aqueous media.

Bangham et al., J. Mol. Biol. 13 (1965), 238–252 observed that phospholipids form superstructures in the presence of water. Depending on physical parameters such as pressure, temperature and ionic concentration, micelles, unilamellar or multilamellar liposomes or even simple lipid double layers form (cf. Liposomes: From physical structure to therapeutic application (1981), Knight, C. G. (ed.), Elsevier, North Holland Biomedical Press, chapter 2: H. Eibl, Phospholipid synthesis, 19–50; chapter 3: F. Szoka and D. Papahadjopoulos, Liposomes: Preparation and Characterization, 51–104). Small unilamellar liposomes are spherical structures with a diameter of 20 to 200 nm (cf. Barenholtz et al., FEBS Let. 99 (1979) 210–214). Their inner volume is comprised of an aqueous medium which is bordered on the outside by the lipid double layer. Depending on their lipophilicity or hydrophilicity, active substances can either be entrapped in the lipid double layer or in the aqueous inner volume of the liposomes and transported and distributed in the organism via the body fluids.

Due to their structure, liposomes serve as a model for membranes in biochemistry and molecular biology. In past years numerous papers on the properties of liposomes and their use as carriers of medicinal agents have also been published (cf. e.g. H. Schreiner and M. Raeder-Schikorr, "Pharmazie in unserer Zeit" 11 (1982), 97–108). Previously published experiments on animals generally show that the liver and spleen dominate over other organs with respect to the uptake of liposomes. About 8% of the liposomes are found in the liver after 1 hour and about 15% after 24 hours.

The possible use of liposomes in medicine is mainly aimed at the selective treatment of diseases. The desired effects of the active substance entrapped in the liposomes should be promoted whereas the undesired effects should be reduced. In this manner it is intended to achieve an improvement in the therapeutic index.

Liposomes are known from DE-OS 40 13 632.9 which contain at least 1 mol % of a compound having a positive excess charge.

However, a disadvantage of administering known liposomes is that their uptake in the liver is relatively limited and that the liposomes can circulate for a long period in the blood. This applies particularly to liposomes which are composed of phospholipids such as lecithin and cholesterol. In this manner the active substance contained in the liposomes is distributed throughout the body which in turn can lead to an increase in the occurrence of undesired side effects of the active substance.

An object of the present invention was therefore to provide new liposomes which exhibit an increased liver uptake compared to liposomes of the state of the art.

This object is achieved by the provision of liposomes which are characterized in that they contain cholesterol, phospholipids and 1 to 14 mol % relative to the total lipid components of the liposomes of one or several compounds of the general formula I

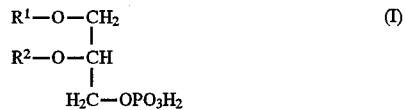

or their salts,
in which $R^1$ and $R^2$ can be the same or different and represent hydrogen, $C_1$–$C_4$ alkyl groups or saturated or unsaturated $C_8$–$C_{24}$ acyl groups which can if desired, be branched or/and substituted provided that at least one of the residues $R^1$ and $R^2$ is an acyl group as defined above.

Under physiological conditions the above compounds (I) are generally in the form of partially protonated anions so that the liposomes according to the invention have a negative excess charge. The amount of negatively charged carrier substances according to formula (I) is generally 1 to 14 mol %, preferably 3 to 10 mol % relative to the total lipid components of the liposomes. An increase in the amount of compounds of formula (I) beyond 15% leads to solubility problems which can go as far as flocculation. Therefore the preferred range is usually adhered to.

Those compounds of formula (I) are preferred in which either both residues represent $C_8$–$C_{24}$ acyl groups or one residue represents hydrogen and the other residue represents a $C_8$–$C_{24}$ acyl group.

Those compounds are particularly preferred in which $R^1$ is a $C_{14}$–$C_{24}$ acyl group and $R^2$ is hydrogen. Preferred examples from this group are in turn 1-stearoyl-sn-glycero-3-phosphoric acid, 1-palmitoyl-sn-glycero-3-phosphoric acid, 1-myristoyl-sn-glycero-3-phosphoric acid and 1-erucoyl-sn-glycero-3-phosphoric acid as well as salts thereof. These phosphatidic acids are preferably used in the form of salts e.g. in the form of monoalkali metal salts, in particular monosodium salts.

In a further particularly preferred class of compounds $R^1$ and $R^2$ are $C_{14}$–$C_{24}$ acyl groups. Preferred examples from this class are in turn 1,2-distearoyl-sn-glycero-3-phosphoric acid, 1,2-dipalmitoyl-sn-glycero-3-phosphoric acid, 1,2-dimyristoyl-sn-glycero-3-phosphoric acid and 1,2-dierucoyl-sn-glycero-3-phosphoric acid as well as salts thereof. These phosphatidic acids are also preferably used in the form of their salts e.g. in the form of their monoalkali metal salts, in particular as monosodium salts.

Surprisingly it was found that a liposome which contains a negatively charged carrier substance according to formula (I) has considerable advantages compared to known liposomes that have been prepared without using compounds according to formula (I).

When liposomes of the state of the art were administered, it was namely found that their uptake in the liver is relatively limited and that they therefore circulate for quite a long period in the blood. In contrast a substantially improved liver uptake was surprisingly found for liposomes according to the invention which in turn leads to a major decrease in the side effects in other organs of the pharmaceutical active substances entrapped in the liposomes.

This was investigated in particular for the anthracyclin antibiotic doxorubicin. This substance has already been used clinically for about 25 years. However, its use as an anti-tumour agent in the treatment of solid tumours, leukaemias and lymphomas (Bonadonna et al., Cancer Res. 30 (1970), 2572–2582; Middleman et al., Cancer 28 (1971), 844–850; Tan et al., Cancer 32 (1973), 9–17) was very limited due to its high cardiac toxicity (Lefrak et al., Cancer 32 (1973), 302–314; Rinehart et al., Ann. Internal. Med. 81 (1974), 475–478; von Hoff et al., Ann. Internal. Med. 91 (1979), 710–717).

In the studies which led to the present invention it was found by experiments on mice that liposomes according to the invention which contain doxorubicin as the active substance have on the one hand a comparable plasma stability to known liposomes but, on the other hand, surprisingly differ greatly from these with regard to pharmacokinetics. When using liposomes according to the invention, considerably smaller amounts of doxorubicin were found in the plasma, in the lung, in the kidney and in particular also in the heart. In contrast in the liver, the desired target organ of the liposomes, a considerably higher concentration of doxorubicin was found when using liposomes according to the invention than when using liposomes of the state of the art or than when using free doxorubicin.

A further surprising advantage of the liposomes according to the invention is that the metabolism of the active substance contained therein differs from the metabolism of an active substance administered without liposomes. Thus when doxorubicin is administered in the form of a commercial preparation (without liposomes), after 1 hour only 20% of the doxorubicin remains in the liver while the rest has already been metabolized. In contrast the administration of the same active substance in the liposomes according to the invention results in 97% of the active substance in a non-metabolized form after 1 hour under otherwise the same conditions so that in this case a metabolism of only 3% occurs. In contrast in the case of commercial preparations (without liposomes) ca. 80% of the active substance has already been metabolized in the liver after 1 hour.

The liposomes according to the invention contain cholesterol and phospholipids as further lipid components in addition to compounds of the general formula (I). The liposomes preferably contain 30 to 50 mol % cholesterol and 49 to 56 mol % phospholipids. Uncharged phospholipids are particularly preferred. The term "uncharged phospholipids" is to be understood as those phospholipids which are uncharged externally (i.e. the term includes those phospholipids which are intramolecular zwitterions). A preferred class of phospholipids in the liposomes according to the invention are phosphoglycerides i.e. compounds that contain a glycerol group in which 2 hydroxyl groups of the glycerol are esterified by fatty acid groups (preferably $C_8$–$C_{24}$ acyl groups) and the third hydroxyl group is esterified by a phosphorylated alcohol. Examples of particularly suitable alcohols are those which carry a positive charge such as ethanolamine and choline. Phospholipids are particularly preferred which are lecithins of the general formula (II)

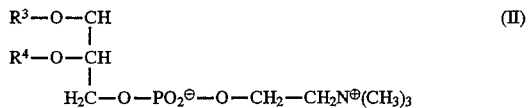

in which $R^3$ and $R^4$ can be the same or different and represent saturated or unsaturated $C_8$–$C_{24}$ acyl groups which if desired, can be branched or/and substituted. $R^3$ and $R^4$ are preferably $C_{14}$–$C_{24}$ acyl groups. $R^3$ and $R^4$ are particularly preferably stearoyl, palmitoyl, myristoyl or erucoyl residues.

The components of the liposomes according to the invention are either commercially available or can be prepared by known processes. Lecithins of formula (II) can for example be prepared according to Woolley and Eibl, Chem. Phys. Lipids 47 (1988), 55–62 and Eibl and Woolley, Chem. Phys. Lipids 41 (1986), 53–63. Furthermore the production of phosphoglycerides is described in DE-OS 32 25 213.7 and the literature references cited therein. Compounds of the general formula (I) can for example be prepared from the respective lecithins by cleaving off the choline residue with phospholipase D (Eibl and Woolley, Methods Enzymol. 72 (1981), 632–639).

In order to produce the liposomes according to the invention, the individual lipid components of the liposomes i.e. 1 to 14 mol % of compounds of the general formula (I) and the other lipid components in an amount which together with compounds of formula (I) amounts to 100 mol %, are dissolved in a suitable solvent, preferably while heating, in order to achieve a homogeneous mixing of the components. The solvent is removed in a vacuum and the finely dispersed lipid film is admixed with an aqueous buffer solution (all solutions that can be used physiologically can be used as the aqueous buffer solution). Subsequently the mixture is kept for ca. 1 hour while stirring gently at a temperature which is generally about 5° C. above the main transition temperature of the lipids e.g. at 50° C.

This pre-heated lipid suspension is then converted by suitable measures in a known manner e.g. in a pressure cell of a French press (Aminco Company, Silverspring, USA) into the liposomes. The French press is composed of a hydraulic press and a standard pressure cell made of steel. After closing the pressure cell, the pressure is increased and the resulting liposome dispersion is pressed under constant pressure through as small outlet. The process is repeated at least three times. After centrifuging the liposome dispersion, the supernatant is removed from the sediment. It contains the liposomes that are now available for various applications and investigations e.g. for the production of liposomes which contain one or several pharmaceutical active substances. The liposomes according to the invention can, however, also be produced by other methods.

The present invention therefore concerns a process for the production of liposomes in which 1 to 14 mol % of compounds of the general formula (I) together with the other lipid components of the liposomes in an amount which together with the compounds of the general formula (I) amounts to 100 mol %, are converted into a lipid suspension, the lipid suspension is pre-heated and the lipid suspension pre-heated in this manner is then converted in a known manner by suitable measures into liposomes.

The present invention in addition concerns a pharmaceutical preparation containing the liposomes according to the invention and one or several pharmaceutical active substances entrapped in the liposomes, if desired, together with common pharmaceutical diluents, auxiliary substances, carrier substances and fillers.

All active substances which can in general be introduced into plasma by means of liposomes can be used as the active substances. Preferred groups of active substances are on the one hand cytostatic agents, in particular anthracyclin antibiotics such as doxorubicin, epirubicin or daunomycin, doxorubicin being particularly preferred. Further preferred cytostatic agents are idarubicin, hexadecylphosphocholine, 1-octadecyl-2-methyl-rac-glycero-3-phosphocholine, 5-fluoruracil, cis-platinum complexes such as carboplatin and novantron.

Further preferred groups of active substances are immunomodulating substances such as cytokines, among these the interferones and in particular α-interferon being particularly preferred, antimycotically active substances (e.g. amphotericin B) and substances active against protozoal diseases (malaria, trypanosomal and Leishmania infections. Taxol is also preferred as an active substance.

In addition the present invention therefore concerns the use of liposomes according to the invention to produce an anti-tumour agent, in which case the active substance is particularly preferably doxorubicin.

The present invention in addition concerns the use of the liposomes according to the invention to produce an agent to influence cell proliferation in which case the active substance is a cytokine, particularly preferably α-interferon.

In order to produce a pharmaceutical composition according to the invention which contains one or several active substances that are entrapped in the liposomes according to the invention, the procedure is as follows:

In order to entrap water-insoluble substances, the active substance is dissolved together with the lipids in a suitable solvent such as methylene chloride or chloroform, subsequently the liposomes are produced according to the process described above.

In order to entrap water-soluble substances, the lipid film is admixed with a solution as described above which, however, now contains the water-soluble active substance. Subsequently, the further procedure is as described above. The supernatant after centrifugation also contains the unentrapped water-soluble active substance in addition to the filled liposomes. This free portion of active substance can be separated from the portion enclosed in the liposomes by for example diafiltration. Before using the liposomes it is preferable to in addition carry out sterile filtration with membrane filters (Sartorius Company, pore diameters 0.2 μm).

The present invention therefore also concerns a process for the production of a pharmaceutical composition in which the process described above is used to produce liposomes and, in order to entrap water-insoluble active substances, the active substance is dissolved together with the lipid components and, in order to entrap water-soluble active substances, the lipid film is admixed with an aqueous solution that contains the water-soluble active substance.

In the following the invention is further elucidated in the examples.

EXAMPLE 1

Production of liposomes 1,2-dipalmitoyl-sn-glycero-3-phosphocholine (DPPC) was obtained from Sygena LTD (Liestal, CH) and cholesterol (Ch) was obtained from Fluka (Buchs, CH). 1,2-distearoyl-sn-glycerol-3-phosphocholine (DSPC) was prepared via 1,2-distearoyl-sn-glycerol (Eibl and Woolley, Chem. Phys. Lipids 41 (1986), 53–63). 1,2-distearoyl-sn-glycero-3-phosphate (DSPA) was produced by hydrolysis of 1,2-distearoyl-sn-glycero-3-phosphocholine using phospholipase D (Eibl and Woolley, Methods Enzymol. 72 (1981), 632–639). Hydrogenated soya phosphatidylinositol (HPI) was prepared from soya lecithin (P5638) that was obtained from "Sigma Chemie GmbH (Steinheim, Germany)". Soya lecithin contains about 10% phosphatidylinositol which was isolated by silica gel chromatography (Woolley and Eibl, Chem. Phys. Lipids 47 (1988), 55–62). The resulting product was hydrogenated in 100 ml $CHCl_3/CH_3OH$ (1:1, v/v) with 10% Pd/C catalyst.

Small unilamellar liposomes having the following compositions (on a molar basis) were produced: DPPC/Ch (6:4); DSPS/DSPA/Ch (5:1:4); DPPC/HPI/Ch (5:1:4). For this 5 mmol of the lipid suspensions were mechanically dispersed in 50 ml citric acid buffer (300 mmol/l, pH 4) for 3 hours in a rotary evaporator at temperatures 5° C. above the phase transition temperature ($T_M$) of the phospholipid with the highest $T_M$. Liposomes were produced from this homogeneous solution using a French press at 20,000 psi. The resulting liposomes were centrifuged for 30 minutes at 30,000 g. 100 mg doxorubicin in powder form was added to this and entrapped at pH 8 using the loading procedure of Mayer et al. (Biochim. Biophys. Acta 857 (1986), 123–126). Free doxorubicin that was not entrapped in the liposomes was removed by diafiltration (Polysulfone Ultrasart Module, exclusion limit 20 kD, Sartocon Mini SM 17521, Sartorius, Germany). All liposomes were sterilized by filtration before use.

EXAMPLE 2

Treatment of mice with liposomes containing doxorubicin

Female NMR-I mice (28–32 g, 6–8 weeks) were obtained from the Animal Breeding Institute, Hannover Germany. The same doses (5.7 mg/kg) were injected in each case into the cordal vein of the mice. Each treatment group was composed of 3 animals. After 1, 24 and 72 hours the mice were anaesthetized with $CO_2$. Blood was collected from the mice by puncture of the heart and stored in heparinized Eppendorf vessels. Tissue samples from the mice (liver, heart etc.) were rinsed in 0.9% NaCl solution and stored at $-70°$ C.

The plasma samples were analyzed by the procedure of Mross et al., (J. Chromatograph. 530 (1990), 192–199). For this 100 μl plasma was loaded onto activated Bond Elut C18 columns (ICT, Frankfurt, Germany) and rinsed with 4 ml buffer (0.02 mol/l Na phosphate, pH 3.9). The columns were dried for 10 minutes at 10 mbar. Doxorubicin and its metabolites were eluted with 4 ml methanol/chloroform (1:1, v/v). The eluate was evaporated to dryness under nitrogen. The residue was taken up in 50 μl (0.02 mol/l Na phosphate/acetonitrile, pH 3.9; 7:3, v/v) and analyzed by means of HPLC using a 4.6 mm×25 cm Merck Lichrocart C 18 RP 5 μm column. The flow rate was 1.5 ml/min. The excitation wavelength was 480 nm and the emission wavelength was 580 nm.

In order to detect doxorubicin and its metabolites in the individual organs, the tissue samples (about 200 mg in each case) were homogenized with a micro-dismembrator (Braun Melsungen AG, Germany). Doxorubicin and its metabolites were treated with an extraction solution at pH 3 (16.5% w/v $AgNO_3$ in acetonitrile/water; 6:4, v/v), in order to release the anthracyclines from a complex with DNA and to precipitate the proteins. After addition of an internal standard (epirubicin) and centrifugation, the supernatant was applied directly to the HPLC column.

The DPPC/Ch liposomes had an average diameter of 64 nm, the DPPC/HPI/Ch liposomes had an average diameter of 91 nm and the DSPC/DSPA/Ch liposomes according to the invention had an average diameter of 88 nm.

The average ratio of doxorubicin to phospholipid was 170 μg/μmol for DPPC/Ch liposomes (95% entrapment), 78 μg/μmol for DSPC/DSPA/Ch liposomes (65% entrapment) and 65 μg/μmol for DPPC/HPI/Ch liposomes (71% entrapment). The three liposome types were stable in plasma for at least 24 hours. Even after 3 months storage at 4° C. no release of doxorubicin from the liposomes could be found.

The dependence of the pharmacokinetics of doxorubicin on the type of formulation is given by the following results: after 1 hour the plasma value was 0.5 μg/ml when free doxorubicin (without liposomes) was added and only traces of doxorubicin could be found after 24 hours. The DPPC/Ch and DPPC/HPI/Ch liposomes exhibited a very high plasma level after 1 hour (59.3 and 42.9 μg/ml respectively) and also exhibited a relatively high level up to 24 hours (5.5 and 4.9 μg/ml respectively). In contrast, only 7.7 μg/ml doxorubicin could be detected in plasma after 1 hour with the DSPC/DSPA/Ch liposomes according to the invention. After 24 hours only traces of doxorubicin could be found.

In the heart the level of free doxorubicin was 13 μg/g after 1 hour whereas with the DSPC/DSPA/Ch liposomes according to the invention only 1.0 μg/g was found. The corresponding values for DPPC/Ch and DPPC/HPI/Ch liposomes were about 3.5 µg/g heart tissue. In the lung and in the kidney considerably lower concentrations of the active substance were also found after 1 hour when doxorubicin was administered in DPPC/DSPA/Ch liposomes compared to the other forms of administration.

Differences in the doxorubicin concentration depending on the form of administration were also found in the liver. After 1 hour the corresponding doxorubicin values were as follows: 11.0 µg/g for free doxorubicin, 42.8 µg/g for the DSPC/DSPA/Ch liposomes according to the invention, 30 µg/g for DPPC/HPI/Ch liposomes and 12.2 µg/g for DPPC/Ch liposomes. The liposomes according to the invention also showed a high value of 25.1 µg/g doxorubicin in the liver even after 24 hours. Even after 72 hours the concentration of doxorubicin in this tissue was still remarkably high.

The following was found concerning the metabolism of doxorubicin in the liver: when free doxorubicin was administered 23% active agent compared to 77% inactive metabolites (aglycones) was found after 1 hour. In contrast, 97% active doxorubicin compared to 3% inactive aglycones was observed for the DSPC/DSPA/Ch liposomes according to the invention. The corresponding values were 96%:4% for DPPC/Ch liposomes and 90%:10% for DPPC/CH liposomes.

As in the liver, an increased uptake of doxorubicin was found in the spleen after 1 hour when using DPPC/DSPA/Ch liposomes.

In summary it was established that the administration of doxorubicin in liposomes according to the invention is superior to the administration of the active substance in a free form and also to the administration of the active substance in other liposomes in particular due to the higher tissue specificity.

What is claimed is:

1. Unilamellar liposomes containing a pharmaceutical active substance, wherein the liposomes contain 30 to 50 mol % cholesterol, 49 to 56 mol % of at least one first phospholipid and 1 to 14 mol % of at least one second phospholipid of the general formula I

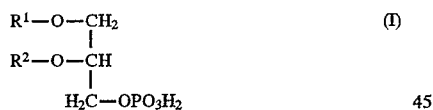

or salts thereof in relation to the total lipid components of the liposomes, in which $R^1$ and $R^2$ are the same or different and represent hydrogen, $C_1$–$C_4$ alkyl groups or saturated or unsaturated $C_8$–$C_{24}$ acyl groups which are unbranched or branched or/and unsubstituted or substituted, provided that at least one of the residues $R^1$ and $R^2$ is an acyl group as defined above, wherein the liposomes are filtered through a filter having a pore diameter of 0.2 µm.

2. Liposomes as claimed in claim 1 wherein the liposomes contain lecithins of the general formula II as the at least one first phospholipid

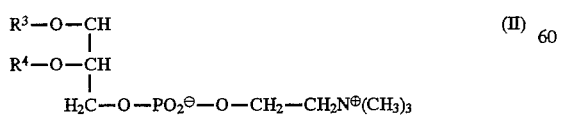

in which $R^3$ and $R^4$ can be the same or different and represent saturated or unsaturated $C_8$–$C_{24}$ acyl groups which are unbranched or branched or/and substituted or unsubstituted.

3. Liposomes as claimed in claim 2, wherein $R^3$ and $R^4$ are $C_{14}$–$C_{24}$ acyl groups.

4. Liposomes as claimed in claim 3, wherein $R^3$ and $R^4$ are selected from the group consisting of stearoyl, palmitoyl, myristoyl and erucoyl residues.

5. Liposomes as claimed in claim 1, wherein the at least one second phospholipid is distearoylphosphatidic acid and the at least one first phospholipid is distearoylphosphocholine.

6. Liposomes as claimed in claim 1, wherein the liposomes contain 3 to 10 mol % of at least one second phospholipid of formula (I) or a salt thereof.

7. Liposomes as claimed in claim 1, wherein $R^1$ is a $C_{14}$–$C_{24}$ acyl group and $R^2$ is hydrogen.

8. Liposomes as claimed in claim 7, wherein, the at least one second phospholipid of formula (I) is selected from the group consisting of 1-stearoyl-sn-glycero-3-phosphoric acid, 1-palmitoyl-sn-glycero-3-phosphoric acid, 1-myristoyl-sn-glycero-3-phosphoric acid and 1-erucoyl-sn-glycero-3-phosphoric acid as well as salts thereof.

9. Liposomes as claimed in claim 8, wherein, the at least one second phospholipid is a monosodium salt of the said acids.

10. Liposomes as claimed in claim 1, wherein, $R^1$ and $R^2$ are $C_{14}$–$C_{24}$ acyl groups.

11. Liposomes as claimed in claim 10, wherein, the at least one second phospholipid is selected from the group consisting of 1,2-distearoyl-sn-glycero-3-phosphoric acid, 1,2-dipalmitoyl-sn-glycero-3-phosphoric acid, 1,2-dimyristoyl-sn-glycero-3-phosphoric acid and 1,2-dierucoyl-sn-glycero-3-phosphoric acid as well as the salts thereof.

12. Liposomes as claimed in claim 11, wherein, the at least one second phospholipid is a monosodium salt of the said acids.

13. Liposomes as claimed in claim 1, wherein, the at least one first phospholipid is a phosphoglyceride.

14. Liposomes as claimed in claim 1, wherein, the liposomes have a diameter of less than 100 nm.

15. Liposomes as claimed in claim 1, wherein the active substance is selected from the group doxorubicin, anthracyclin antibiotic, idarubicin, carboplatin, taxol and cytokine.

16. A process for the production of unilamellar liposomes containing a pharmaceutical active substance, wherein the liposomes contain 30 to 50 mol % cholesterol, 49 to 56 mol % of at least one first phospholipid and 1 to 14 mol % of at least one second phospholipid of the general formula I

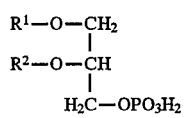

or salts thereof in relation to the total lipid components of the liposomes, in which $R^1$ and $R^2$ are the same or different and represent hydrogen, $C_1$–$C_4$ alkyl groups or saturated or unsaturated $C_8$–$C_{24}$ acyl groups which are unbranched or branched or/and unsubstituted or substituted, provided that at least one of the residues $R^1$ and $R_2$ is an acyl group as defined above, the process comprising:

(a) dissolving the at least one second phospholipid of the general formula I, the cholesterol and the at least one first phospholipid in a solvent, wherein the at least one first phospholipid of general formula I, the cholesterol and the at least one second phospholipid amount to 100 mol %, (b) removing the solvent in a vacuum to produce a finely dispersed lipid film, (c) mixing the finely dispersed lipid film with an aqueous buffer solution to form a lipid suspension, wherein the aqueous buffer solution comprises the pharmaceutical active substance, (d) heating the lipid suspension, and (e) forming liposomes from the lipid suspension of step (d) whereby liposomes containing the pharmaceutical active substance are produced, and thereafter filtering the liposomes through a filter having a pore diameter of 0.2 μm.

17. The process as claimed in claim 16, wherein the pharmaceutical active substance is water-soluble.

18. The process as claimed in claim 16, further comprising:

(f) separating the liposomes of step (e) from the lipid suspension of step (e).

19. A process for the production of unilamellar liposomes containing a water-insoluble pharmaceutical active substance, wherein the liposomes contain 30 to 50 mol % cholesterol, 49 to 56 mol % of at least one first phospholipid and 1 to 14 mol % of at least one second phospholipid of the general formula I

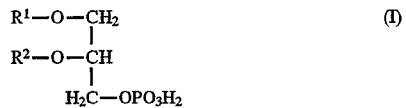

or salts thereof in relation to the total lipid components of the liposomes, in which $R^1$ and $R^2$ are the same or different and represent hydrogen, $C_1$–$C_4$ alkyl groups or saturated or unsaturated $C_8$–$C_{24}$ acyl groups which are unbranched or branched or/and unsubstituted or substituted, provided that at least one of the residues $R^1$ and $R^2$ is an acyl group as defined above, the process comprising:

(a) dissolving the at least one of second phospholipid of the general formula I, the cholesterol, the at least one first phospholipid and the water-insoluble active substance in a solvent, wherein the at least one second phospholipid of general formula I, the cholesterol and the at least one first phospholipid amount to 100 mol %, (b) removing the solvent in a vacuum to produce a finely dispersed lipid film, (c) mixing the finely dispersed lipid film with an aqueous buffer solution to form a lipid suspension, (d) heating the lipid suspension, and (e) forming liposomes from the lipids suspension of step (d) whereby liposomes containing the water-insoluble active substance are produced, and thereafter filtering the liposomes through a filter having a pore diameter of 0.2 μm.

* * * * *